United States Patent
Chen et al.

(10) Patent No.: US 6,972,564 B2
(45) Date of Patent: Dec. 6, 2005

(54) OBJECTIVE ORIENTED METHODS FOR NMR LOG ACQUISITIONS FOR ESTIMATING EARTH FORMATION AND FLUID PROPERTIES

(75) Inventors: Songhua Chen, Katy, TX (US); Carl M. Edwards, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 125 days.

(21) Appl. No.: 10/288,115

(22) Filed: Nov. 5, 2002

(65) Prior Publication Data

US 2003/0107374 A1 Jun. 12, 2003

Related U.S. Application Data

(60) Provisional application No. 60/332,888, filed on Nov. 6, 2001.

(51) Int. Cl.$^7$ .................................................. G01V 3/00
(52) U.S. Cl. ...................................... 324/303; 324/306
(58) Field of Search ............................... 324/303, 300, 324/306, 307, 318, 322

(56) References Cited

U.S. PATENT DOCUMENTS

| | | | |
|---|---|---|---|
| 5,023,551 A | 6/1991 | Kleinberg et al. | 324/303 |
| 5,363,041 A | 11/1994 | Sezginer | 324/303 |
| 5,412,320 A | 5/1995 | Coates | 324/303 |
| 5,557,200 A | 9/1996 | Coates | 324/303 |
| 5,585,720 A | 12/1996 | Edwards | 324/309 |
| 5,596,274 A | 1/1997 | Sezginer | 324/303 |
| 5,696,448 A | 12/1997 | Coates et al. | 324/303 |
| 5,796,252 A | 8/1998 | Kleinberg et al. | 324/303 |
| 5,936,405 A | 8/1999 | Prammer et al. | 324/303 |
| 6,023,163 A | 2/2000 | Flaum et al. | 324/303 |
| 6,049,205 A | 4/2000 | Taicher et al. | 324/303 |
| 6,051,973 A | 4/2000 | Prammer | 324/303 |
| 6,069,477 A | 5/2000 | Chen et al. | 324/303 |
| 6,097,184 A | 8/2000 | Flaum | 324/303 |
| 6,163,153 A | 12/2000 | Reiderman et al. | 324/314 |
| 6,242,912 B1 | 6/2001 | Prammer et al. | 324/303 |
| 6,291,995 B1 | 9/2001 | Speier et al. | 324/303 |
| 6,331,775 B1 | 12/2001 | Thern et al. | 324/303 |
| 6,346,813 B1 | 2/2002 | Kleinberg | 324/303 |
| 6,366,087 B1 | 4/2002 | Coates et al. | 324/303 |
| 6,396,567 B1 | 5/2002 | Chu et al. | 355/69 |
| 6,452,389 B1 * | 9/2002 | Edwards | 324/303 |
| 6,600,316 B2 * | 7/2003 | Chen et al. | 324/303 |

OTHER PUBLICATIONS

M.N. Miller et al.; *Spin Echo Magnetic Resonance Logging: Porosity and Free Fluid Index Determination*, SPE 20561, 65th Annual Technical Conference and Exhibition of the Society of Petroleum Engineers, Sep. 23–26, 1990, pp. 321–334, 19 Figs., Fig. A1–A2.

* cited by examiner

Primary Examiner—Louis Arana
(74) Attorney, Agent, or Firm—Madan, Mossman & Sriram, P.C.

(57) ABSTRACT

An objective oriented NMR logging method selects pulse sequences over a plurality of frequencies from a set of building blocks. The building blocks include trainlet sequences wherein each trainlet comprises an excitation pulse and a plurality of refocusing pulses, the total length of a trainlet being typically less than 10 ms. Another building block is a short CPMG or modified CPMG sequence and yet another building block is a regular CPMG or modified CPMG sequence. The modified CPMG sequences may have refocusing pulses with a tipping angle less than 180° to reduce the power consumption. Based on the logging objective (formation evaluation or FE, FE plus hydrocarbon typing, FE plus gas evaluation) the building blocks are combined at a plurality of frequencies with different wait times and TEs.

51 Claims, 14 Drawing Sheets

$TW_N = 30\ ms$ $$mean = \sum_i NS_i \cdot block_i \Big/ \sum_i NS_i$$

OBJECTIVE ORIENTED METHODS FOR NMR LOG ACQUISITIONS FOR ESTIMATING EARTH FORMATION AND FLUID PROPERTIES

CROSS-REFERENCES TO RELATED APPLICATIONS

This application claims priority from U.S. Provisional Patent Application Ser. No. 60/332,888 filed on Nov. 6, 2001.

BACKGROUND OF THE INVENTION

1. Field of the Invention

This invention is related to methods for acquiring nuclear magnetic resonance (NMR) measurements for determination of petrophysical properties of formations and properties of fluids therein. Specifically, the invention deals with an objective oriented method for acquisition of NMR data.

2. Description of the Related Art

Nuclear magnetic resonance is used in the oil industry, among others, and particularly in certain oil well logging tools. NMR instruments may be used for determining, among other things, the fractional volume of pore space and the fractional volume of mobile fluid filling the pore space of earth formations. Methods of using NMR measurements for determining the fractional volume of pore space and the fractional volume of mobile fluids are described, for example, in "Spin Echo Magnetic Resonance Logging: Porosity and Free Fluid Index Determination," M. N. Miller et al., Society of Petroleum Engineers paper no. 20561, Richardson, Tex., 1990. Further description is provided in U.S. Pat. No. 5,585,720, of Carl M. Edwards, issued Dec. 17, 1996 and having the same assignee as the present application, entitled "Signal Processing Method For Multi-exponentially Decaying Signals And Applications To Nuclear Magnetic Resonance Well Logging Tools." The disclosure of that patent is incorporated herein by reference.

Deriving accurate relaxation spectra from nuclear magnetic resonance (NMR) data from logging subterranean formations is critical to determining total and effective porosities, irreducible water saturations, and permeabilities of the formations. U.S. Pat. No. 6,069,477 to Chen et al having the same assignee as the present application discusses the constituents of a fluid saturated rock and various porosities of interest. Referring to FIG. 1, the solid portion of the rock is made up of two components, the rock matrix and dry clay. The total porosity as measured by a density logging tool is the difference between the total volume and the solid portion. The total porosity includes clay-bound water (CBW), capillary bound water (also known as Bulk Volume Irreducible or BVI), movable water and hydrocarbons. The effective porosity, a quantity of interest to production engineers, is the sum of the last three components and does not include the clay bound water. Accurate spectra are also essential to estimate the irreducible and the movable fluid volumes; distortion of partial porosity distributions that has been commonly observed for a variety of reasons, affects the estimates of these quantities. The reasons for the distortions to occur are mainly due to poor signal-to-noise ratio (SNR) and poor resolution in the time domain of the NMR data.

The most common NMR log acquisition and core measurement method employs $T_2$ measurements using CPMG (Carr, Purcell, Meiboom and Gill) sequence, as taught by Meiboom and Gill in "Modified Spin-Echo Method for Measuring Nuclear Relaxation Time," Rev. Sci. Instrum. 1958, 29, pp. 688–691. In this method, the echo data in any given echo train are collected at a fixed time interval, the interecho time (TE). Depending on the relaxation rate of the nuclear species under investigation in the underlying system, usually, a few hundred to a few thousand echoes are acquired to sample relaxation decay. Determining a light oil component, which has long relaxation time, requires taking several hundreds of ms of data while determination of CBW, which decays very fast, can be done with echo sequences of as few as ten echoes.

There are numerous examples of NMR logging techniques used for obtaining information about earth formations and fluids. In measurement-while-drilling (MWD) operation, measurements are made while the wellbore is being drilled while in wireline logging, measurements are made after a wellbore has been drilled. The logging tools are lowered into the borehole and NMR signals are obtained using different configurations of magnets, transmitter coils and receiver coils. A static magnetic field is produced in the formation using permanent or electro-magnets. The static field aligns nuclear spins within the formation parallel to the static field. A pulsed RF field is applied using a transmitter on the logging tool and the evolution of the nuclear magnetization signals produced by the pulsed RF field are analyzed to determine formation properties. The prior art shows different radio frequency (RF) pulsing schemes for generating RF fields in the formation. The most commonly used pulsing schemes are variations of the CPMG sequence denoted by $$(TW_i, 90_{\pm \pi/2}, (\tau, 180, \tau, \text{echo})_j)_i \quad (1)$$

where TW is a wait time, 90 is a tipping pulse that tips the nuclear spins by an angle substantially equal to 90°, 180 is a refocusing pulse that tips the nuclear spins by an angle substantially equal to 180°, and echo is a spin echo. The time interval between successive refocusing pulses is $2\tau$, j is the number of echoes, and i denotes repetitions of the basic pulse sequence. A variation of the CPMG sequence is taught in U.S. Pat. No. 6,163,153 to Reiderman in which the use of a refocusing pulse with a tipping angle less than 180° is disclosed.

Rig time is expensive, so that the general objective in wireline logging is to obtain interpretable data within as short a time as possible. In MWD logging, on the other hand, no additional rig time is involved. However, when more measurements can be acquired in a given time, the data quality can be improved. The parameters that may be varied are the acquisition frequencies and the number of different frequencies, the tip angles, the wait time, the number of pulses within a CPMG sequence, and the time interval between the pulses. Long wait times are needed for proper evaluation of formation fluids that have long relaxation times, e.g., gas reservoirs while short wait times and/or short pulse spacings are used for evaluating faster relaxing components, e.g., irreducible fluid (BVI) and clay bound water (CBW). For example, U.S. patent application Ser. No. 09/396,286 of Thern et al, now U.S. Pat. No. 6,331,775 and having the same assignee as the present application discusses the use of a dual wait time acquisition for determination of gas saturation in a formation. U.S. Pat. No. 5,023,551 to Kleinberg et al discusses the use of CPMG sequences in well logging. U.S. Pat. No. 6,069,477 to Chen et al teaches the use of pulse sequences with different pulse spacings to determine CBW. Phase alternated pairs (PAPs) of sequences are commonly acquired to reduce the effects of ringing and DC offset.

When, as is commonly the case, the logging tool has a static field gradient, acquisition may be speeded up by overlapping the acquisition at different frequencies. Examples of this are given in Taicher (U.S. Pat. No. 6,049, 205) and in co-pending US patent application Ser. No. 09/863,568 of Chen et al.

An example of a prior art NMR wireline logging tool is the device used by Numar Corporation under the service mark MRIL®. This may be operated at nine different frequencies with different options for parameters of the pulse sequence described above. Proper selection of these operating parameters requires a knowledge of the effect of the parameters on the acquired data as well as on how the acquired data could be processed to give petrophysical and formation fluid parameters of interest. Without extensive training, engineers at the wellsite are usually not qualified to make this selection and consequently, NMR logging has usually been carried out with preselected operating parameters with little opportunity for modification in view of conditions encountered at the wellsite. The engineer at the wellsite, however, often knows a priori the fluids that may be encountered and can commonly make qualitative evaluations of the formation types and the fluids encountered downhole (e.g., based on drill cuttings and/or other logs) and decide on what kind of information is needed from the NMR logs. It would be desirable to have a method in which a minimal amount of specification of NMR logging parameters is required at the wellsite as long as the logging objectives are specified by the engineer at the wellsite. Such an invention should preferably be able to adjust the acquisition depending upon actual downhole conditions. The present invention satisfies this need.

SUMMARY OF THE INVENTION

The present invention is an objective oriented method of using a multifrequency NMR logging tool for obtaining parameters of earth formations and/or fluids therein. It enables a wellsite engineer with little knowledge of NMR logging to acquire NMR logs with a comprehensive logging program suitable for defined objectives. Based on the objective, the method selects an acquisition sequence of at least two of three building blocks of pulse sequences, each of the at least three building blocks including an excitation pulse and a refocusing pulse. The acquisition sequence is distributed over a plurality of frequencies and is used for pulsing a radio frequency (RF) antenna on the logging tool and subsequently generating spin echo signals from the formation. A building block is designed to achieve a specific logging objective, which is part of the overall objectives for an NMR logging. Thus, a combination of multiple building blocks that forms a comprehensive logging program achieves a defined set of logging objectives. An example of a building block is a trainlet sequence including with a short interval between the trainlets. Another example of a building block is a so-called regular sequence that may be a CPMG sequence or a modified CPMG sequence having a refocusing angle between 90° and 180°.

When the objective is formation evaluation, the properties that may be determined include one or more of (i) total porosity, (ii) clay bound water, (iii) effective porosity, (iv) bound volume irreducible, and (v) permeability. In a preferred embodiment of the invention, at least three frequencies are used. The number of frequencies used is based on the T1 of the formation and the desired vertical resolution. Particular ones of the formation parameters may be determined using only a subset of the acquired data. Phase alternated pairs of sequences may be used to reduce ringing and baseline effects. Additional frequencies may also be used.

When the objective is formation evaluation and hydrocarbon evaluation, in a preferred embodiment of the invention, at least four frequencies are used and data are acquired with building blocks comprising trainlets and regular sequences having multiple TE and TW. The number of TE and TW vary according to the hydrocarbon types.

When the formation includes dry gas or other fluids that have significantly long spin-lattice relaxation time T1, long sequences are required to fully evaluate the gas saturation. The method of the invention then uses sub-sequences over multiple frequencies for obtaining data primarily related to formation evaluation and additional sequences with long wait times are interspersed between the sub-sequences.

BRIEF DESCRIPTION OF THE DRAWINGS

FIG. 4b shows the results of combining the three sets of data in FIG. 4a.

DETAILED DESCRIPTION OF THE INVENTION

The method of the present invention may be used with any suitable NMR logging tool. An example of such a tool is given in U.S. Pat. No. 4,710,713 to Taicher et al, the contents of which are incorporated herein by reference. It is to be noted that the Taicher device is for exemplary purposes only, and that the method of the present invention may be used with any gradient logging tool capable of being operated at more than one frequency.

Figure 2A:
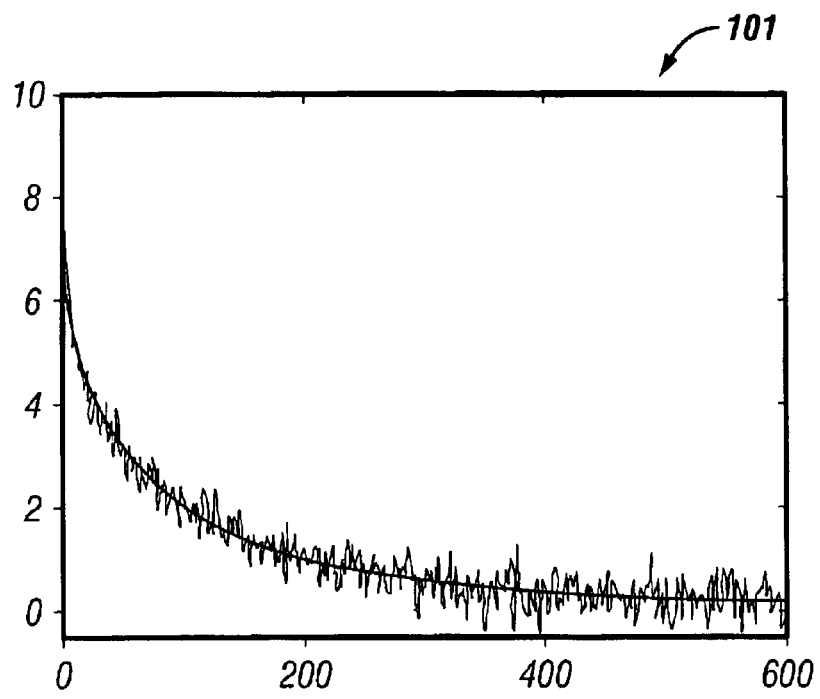
FIGS. 2a, 2b (Prior art) schematically show the determination of relaxation times from NMR data.
Figure 2B:
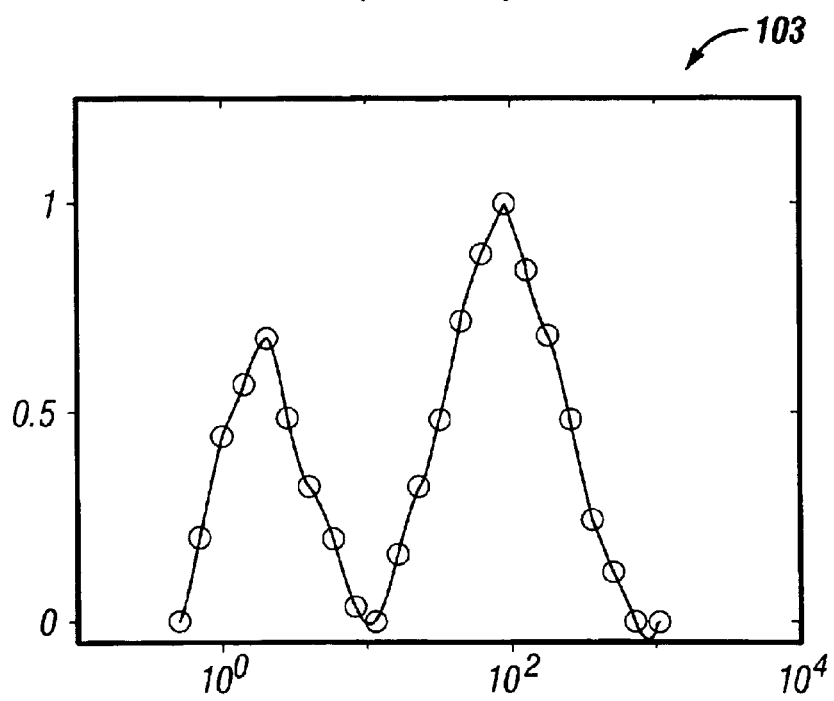

The present invention comprises a number of basic building blocks (discussed below) that make possible an objective oriented NMR data acquisition. One of the many end results of NMR data acquisition and processing is schematically illustrated in FIGS. 2a, 2b. FIG. 2a shows an example of an NMR pulse echo train and a curve 101 fit to the data that comprises a number of exponentials. The abscissa in FIG. 2a is time and the ordinate is the amplitude of the echo. The result of inversion (or other analysis) of the data in FIG. 2a is a distribution of relaxation times 103 that, in the example shown, are the transverse relaxation times of the nuclear spins. The individual points along the curve 103 characterize the components of the multiexponential fit to the data in FIG. 2a. Note that it is common practice to plot the distribution of relaxation times on a logarithmic scale.

Figure 1:
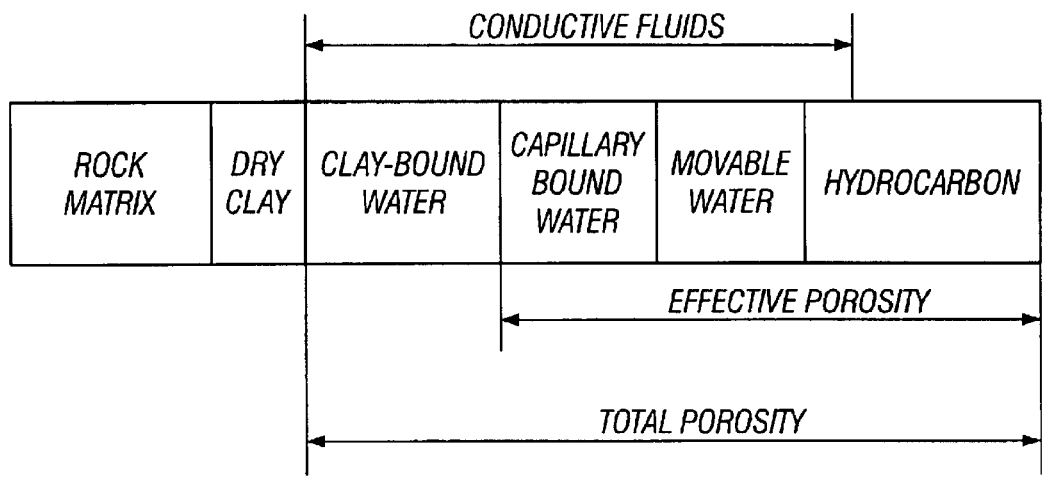
FIG. 1 shows the different constituents of a fluid filled rock.
Figure 3:
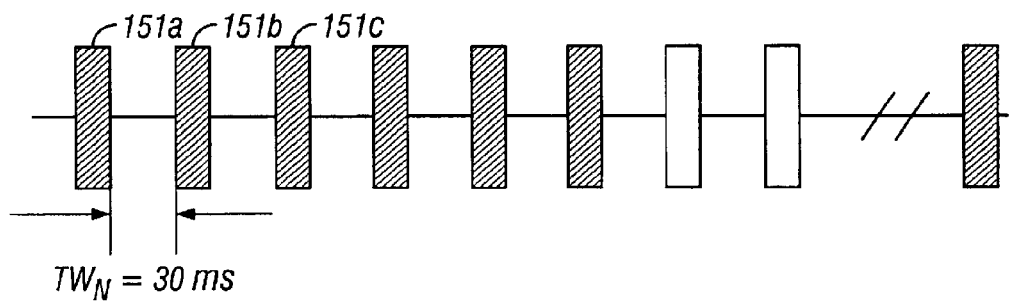
FIG. 3 illustrates one of the building blocks in the method of the present invention, a sequence of trainlets.

One building block in the present invention is schematically illustrated in FIG. 3. Shown are a plurality of trainlets 151a, 151b, 151c . . . that are separated by a wait time $TW_n$ that may be of the order of 30 ms. The use of fast repetition of partially polarized echo trainlets boosts SNR of the early echoes, which is critical to the estimate fast-relaxing components, such as those associated with clay bound water, CBW. The wait time of 30 ms is sufficient for the CBW components which have T2 relaxation times shorter than 4 ms, and which also have a typical T1/T2 ratio of <2.5. A similar treatment is applicable to improve BVI components. The use of these short trainlets is discussed next with reference to FIGS. 4a and 4b.

Figure 4A:
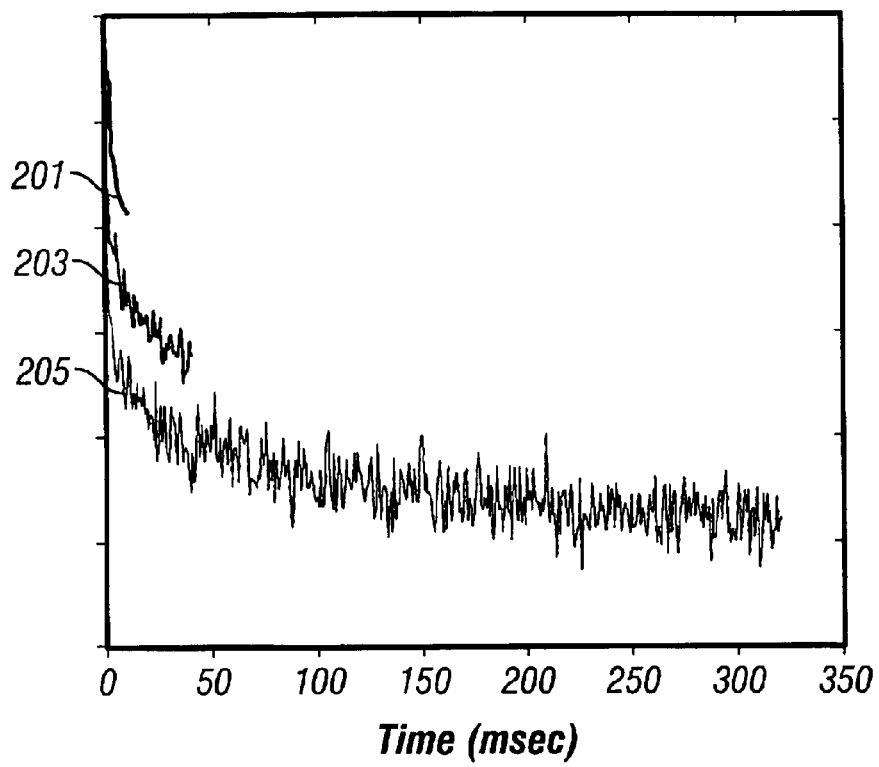
FIG. 4a shows data acquired with a regular sequence, a short sequence and an average of trainlets.
Figure 4B:
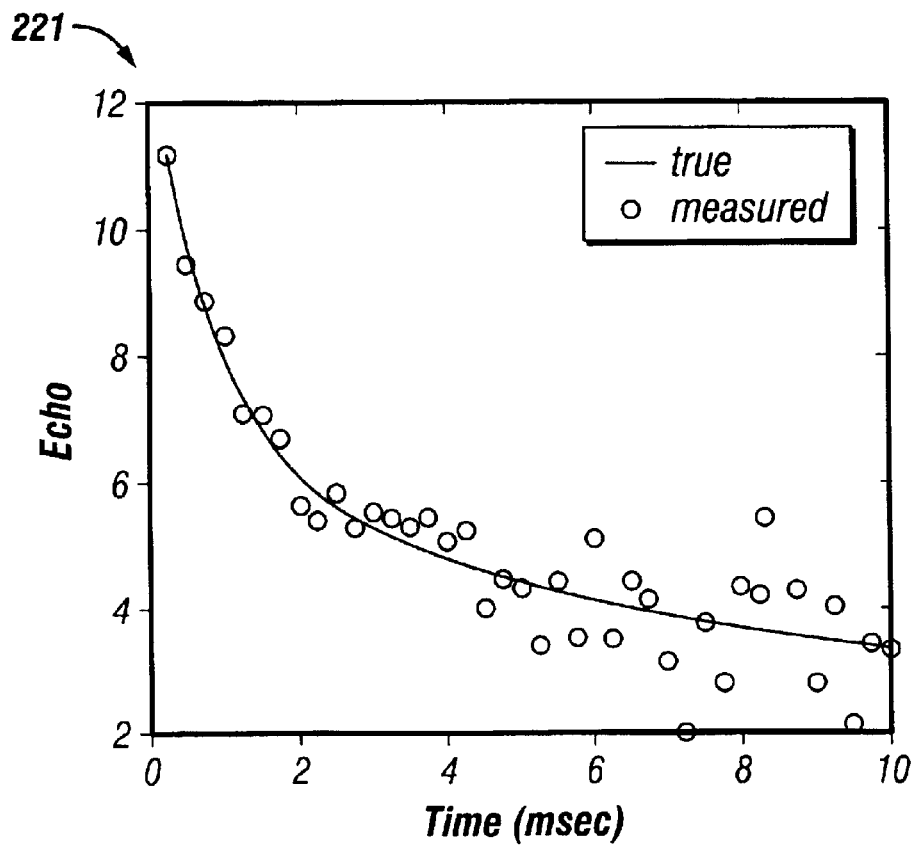

Turning now to FIG. 4a, three curves are shown. 205 is an example of a single echo sequence approximately 325 ms long and shows a noisy signal, which already includes an averaging of N samples. From the standpoint of characterizing 205 by a combination of exponentials, the noise at the early times (<10 ms) is particularly troublesome as these correspond to the rapidly relaxing components of the $T_2$ relaxation spectrum. The curve 203 corresponds to averaging a number of 4N, short acquisition sequences 50 ms long while the curve 201 corresponds to averaging many 24N trainlets each 10 ms long. The curves 201, 203 and 205 are shown vertically displaced for clarity. In a preferred embodiment, simultaneous inversion is applied to all these data. In another embodiment, one of more of these data is used to obtain one of the formation evaluation objectives. This implementation, is, is one step closer to an ideal signal, which is the continuous noise reduction towards the early echoes, such as that shown in FIG. 4b.

Figure 5:
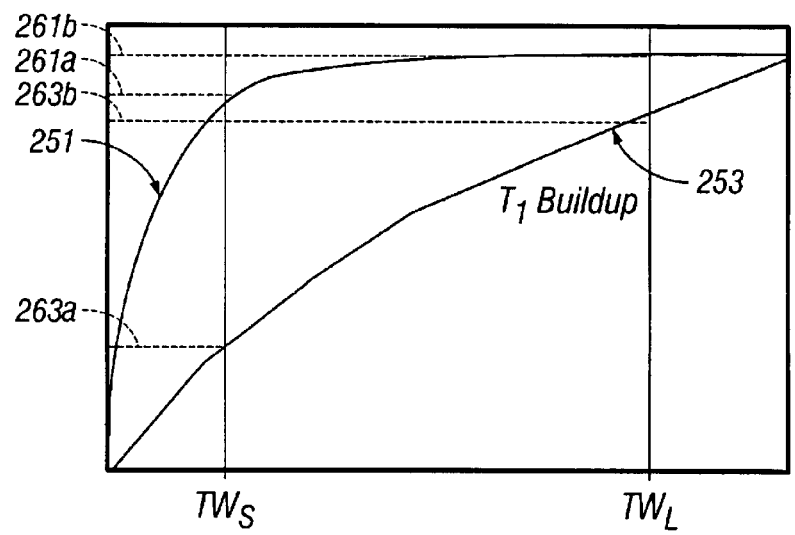
FIG. 5 schematically shows the polarization of spins of water and hydrocarbons as a function of wait time.

Turning now to FIG. 5, the effect of another building block in NMR pulse echo acquisition is illustrated. Shown schematically in FIG. 5 is the polarization of water 251 and hydrocarbon 253 in a static magnetic field as a function of time. For two selected wait times denoted by $TW_L$ and $TW_S$, it can be seen that the polarization of water differs only slightly (compare 261a with 261b) while the polarization of hydrocarbons differs significantly (compare 263a with 263b). The spin echo signals following two different wait times are thus a useful diagnostic of hydrocarbon and water saturation in the formation. This is discussed in Thern and in U.S. Pat. No. 5,497,087 to Vinegar et al.

Another building block that is included in the present invention is based upon the effect of changing the interval TE between the refocusing pulses. The basic equation describing the transverse relaxation of magnetization in fluid saturated porous media is $$M(t) = \int_{T_{2min}}^{T_{2max}} P(T_2)e^{-t/T_2} dT_2 \qquad (2)$$

where M is magnetization, and effects of diffusion in the presence of a magnetic field gradient have not been taken into consideration. Eq.(1) is based on the assumption that diffusion effects may be ignored. In a gradient magnetic field, diffusion causes atoms to move from their original positions to new ones, which causes these atoms to acquire different phase shifts compared to atoms that did not move. This contributes to additional decay of magnetization, resulting in a faster rate of apparent relaxation.

The effect of field gradients is given by an equation of the form $$\frac{1}{T_2} = \frac{1}{T_{2bulk}} + \frac{1}{T_{2surface}} + \frac{1}{T_{2diffusion}} \qquad (3)$$

where the first two terms on the right hand side are related to bulk relaxation and surface relaxation while the third term is related to the field gradient G by an equation of the form $$T_{2diffusion} = \frac{C}{TE^2 \cdot G^2 \cdot D} \qquad (4)$$

where TE is the interecho spacing, C is a constant and D is the diffusivity of the fluid. The diffusivity of gas is greater than that of liquid hydrocarbons and of water. Consequently, according to eq. (3), for a given TE and G, the $T_{2diffusion}$ of gas is less than that of liquid hydrocarbons and gas and consequently, the effect on the $T_2$ according to eq. (2) will be greater. This effect may be used to identify gas in reservoirs and to estimate the gas saturation of a reservoir.

Figure 6A:
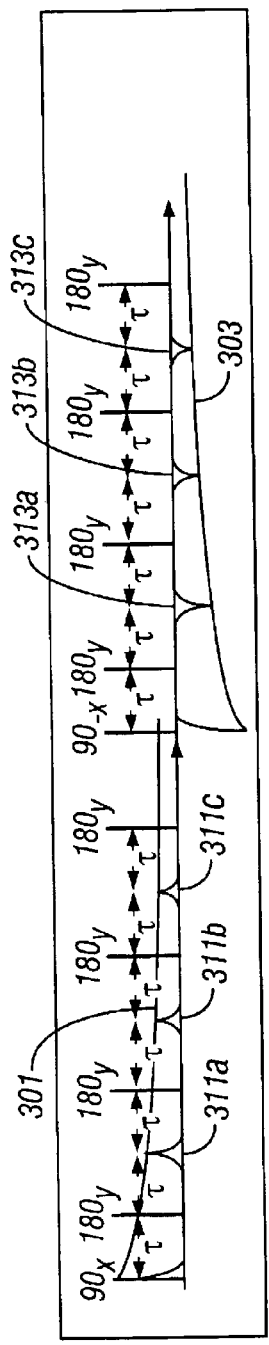
FIGS. 6a and 6b schematically show the use of phase alternated pairs (PAP) of sequences at a single frequency and two frequencies.
Figure 6B:
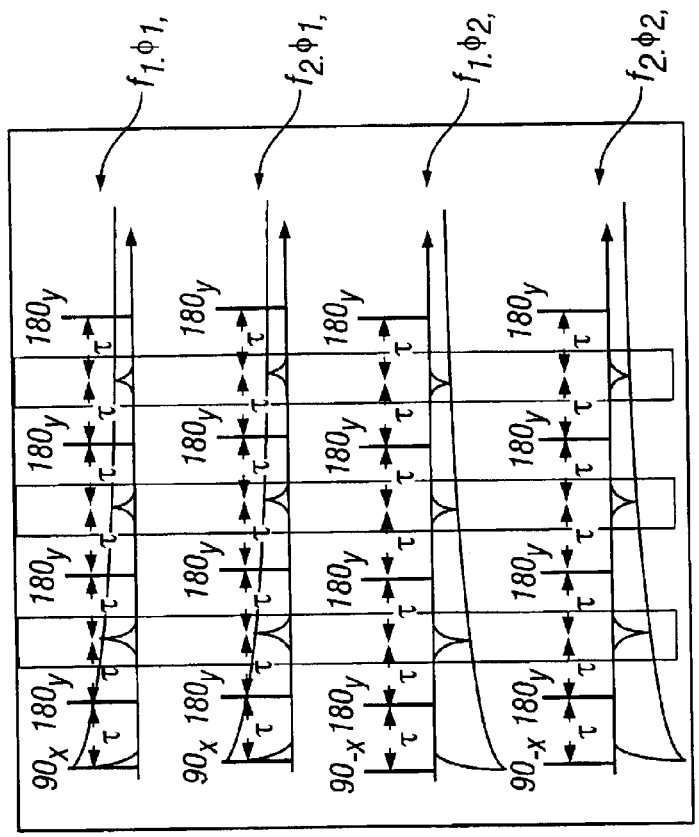

Phase alternating pair design (PAP) is integrated within a building block, if the building block contains more than one trainlet and includes an even number of trainlets (FIG. 6a). This implementation will allow less cross-depth-range averaging resulting in a better vertical resolution. Otherwise, PAP is integrated with a cycling order illustrated in FIG. 6b, which is a conventional phase alternated pair (PAP) sequence of pulses. In FIG. 6a, the first 90° tipping pulse denoted by $90_x$ is followed by a sequence of refocusing pulses denoted by $180_y$ giving rise to a series of pulse echoes 311a, 311b, 311c . . . having a decay curve denoted by 301. This is followed by a second 90° tipping pulse denoted by $90_{-x}$ (i.e., with a phase opposite that of the first tipping pulse) and another series of refocusing pulses 313a, 313b, 313c, . . . having a decay curve denoted by 303. Data from the two echo trains when properly combined (summing or subtracting, depending on the sign convention used) gives a single echo train in which the DC offset and ringing effects are substantially attenuated. This approach is impractical if full polarization is required because overall acquisition time is approximately twice that of a single echo sequence; however it is acceptable and preferred for trainlets because a very short TW is used. FIG. 6b shows the use of conventional PAP sequences when a multifrequency tool is used and when TW is long. An illustrative example is shown for two frequencies. The top sequence in FIG. 6b corresponds to a first frequency $f_1$ with a phase denoted by $\phi_1$. The next sequence in FIG. 6b corresponds to a second frequency $f_2$ with a the same phase denoted by $\phi_1$. The next two sequences corresponds to the first frequency and the second frequency with a second phase denoted by $\phi_2$. The transmitter is able to cycle through the two frequencies and the two phases in a time only slightly greater than that needed for a single frequency acquisition in FIG. 6a. By proper selection of the frequencies and the shapes of the tipping and refocusing pulses, the interference between adjacent frequency bands can be substantially reduced. Such a pulse shaping is taught in co-pending U.S. patent application Ser.

No. 09/606,998 of Beard et al, having the same assignee as the present application.

In prior art methods, the PAP processing is used only with two identical acquisitions, i.e., the two echo trains involved in PAP processing are acquired with a same frequency, TE, TW, etc. In the method of the present invention, this stringent requirement of identical echo trains is significantly relaxed. Ringing and DC offset noises depend primarily on TE, frequency, and pulse characteristics, but are not affected by the wait time. The wait time, TW, affects only the signal strength. Therefore, it is possible to combine two echo trains that are acquired with different TW as long as other acquisition parameters are identical. For multiple-frequency data acquisitions, this revision permits more flexible echo train combination. Prior art PAP methods require at least two samples of the entire sequence package: this could take more than 10 seconds. With the present invention, some petrophysical information can be obtained within a single sample of the entire sequence, resulting in a better vertical resolution. This is particularly useful in high resolution CBW and/or BVI estimation. The logging speed for CBW and/or BVI acquisition may be selected to provide such high resolution.

One acquisition sequence that may be synthesized in the present invention with the building blocks described above is the so-called formation evaluation (FE) sequence. This is a simplified acquisition that satisfies several different demands. These include the determination of BVI (Bound volume irreducible), BW (Bound water) and TP (total porosity) or EP (Effective Porosity). The BW and BVI determinations are made with high-resolution, something that is desired for integration with other logs. The TP determination is made with standard resolution and the SNR of early echoes for the early echoes that are most critical for BVI and porosity determination are improved.

Figure 7:
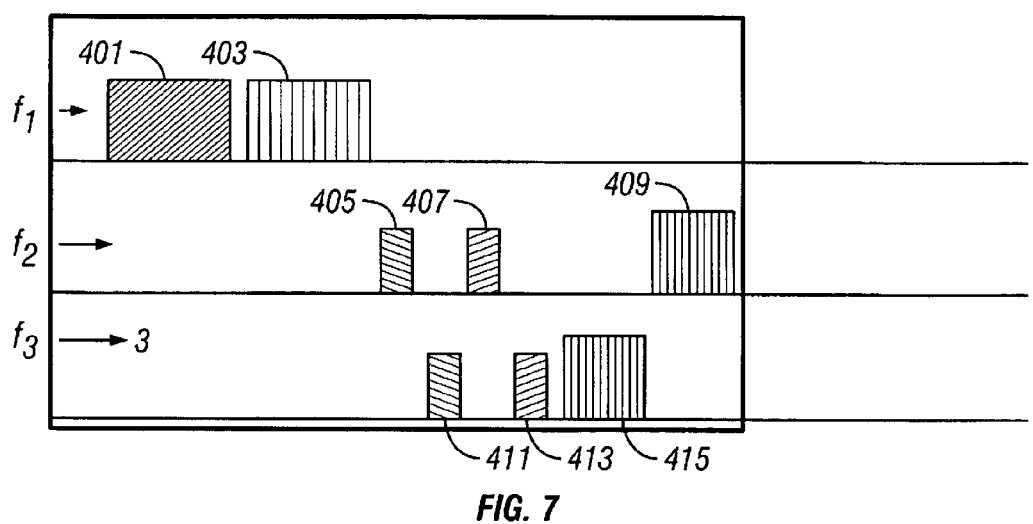
FIG. 7 schematically shows an example of a three frequency embodiment of the present invention for formation evaluation.
Figure 8:
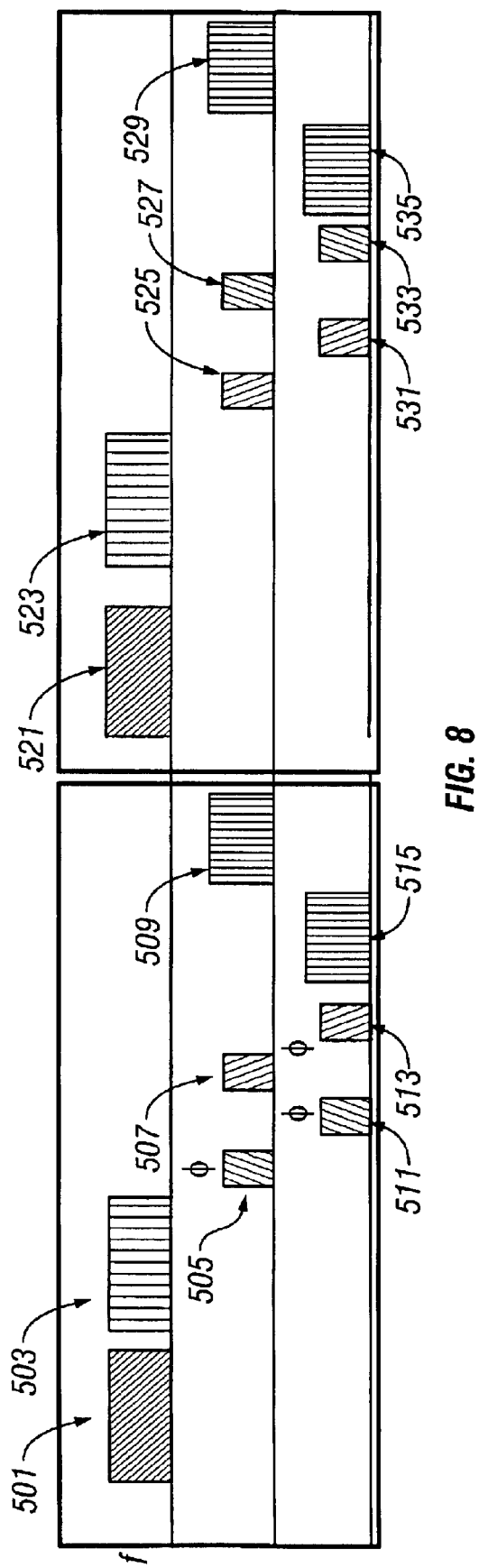
FIG. 8 shows a PAP embodiment at three frequencies for the example of FIG. 7.

Turning now to FIG. 7, an example of a component of three frequency FE acquisition is shown. The block 401 represents a single CPMG sequence (or modified CPMG sequence with shortened refocusing pulse) at a first frequency $f_1$. This is referred to hereafter as a regular sequence. In a preferred embodiment of the invention, the sequence has a $TE_1$, range from 0.2–1.0 ms with a total length of 0.5–1.0 s. The block 403 represents a series of trainlets with a $TE_2$ being the shortest possible value by the instrument, usually in 0.2–0.5 ms range, $NE_2*TE_2\sim 8$ ms, TW~30 ms, and number of trainlets NS>>1. This is acquired at the same frequency as block 401 and the phase is alternated between successive trainlets. This is referred to hereafter as a trainlet sequence. The block 405 at a second frequency $f_2$ comprises a short CPMG (or modified CPMG) sequence with $TE_3$ preferably selected to be the same as $TE_1$, $NE_3*TE_3\sim 40$ ms, that are fully polarized. This is referred to hereafter as a short sequence. The block 407 at the second frequency $f_2$ comprises a short sequence similar to 405 with $TE_3$ and identical acquisition length $NE_3*TE_3\sim 40$ ms, that are only partially polarized (Note the short wait time between the end of 405 and the beginning of 407) and that has a phase that is reversed relative to the phase of 405. The next component at the second frequency $f_2$ is the block 409 that is similar to block 403 but does not necessarily contain same number of trainlets, NS. Moving to the third frequency $f_3$, shown are blocks 411 and 413 that are similar to 405 and 407, respectively (i.e., short CPMG sequences with a long and short wait time respectively, polarity flipped between 411 and 413) and a block 415 similar to 409. The pulse sequences shown in FIG. 7 may then be repeated at the three frequencies with the phase flipped. This is shown in FIG. 8 where for simplifying the illustration, the reversal of phase between the first and second block is not shown. If the reservoir fluid system's $T_1$, is short such that the time used to acquire 405–409 (or 401–402, whichever is shorter) is sufficient to effectively polarize all protons, no additional time is required to wait between the repeats. If, on the other hand, this time period is insufficient for full polarization, the repetition may be at additional frequencies $f_4$, $f_5$ and $f_6$, shown in FIG. 9. Again, for simplifying the illustration, the phase alternation is not shown. The sequences illustrated in FIG. 7 may be expanded to 6, 9 or 12 frequencies, depending upon the formation fluid $T_1$ characteristics and the logging speed. In a preferred embodiment of the invention, the number of frequencies is automatically determined on the basis of the desired wait time TW. To optimize the vertical resolution under a given logging speed, the minimal number of multiplicity of 3 frequencies (i.e., 3, 6, 9, . . . ) that is sufficient to achieve full polarization of formation fluids is automatically chosen.

Figure 10A:
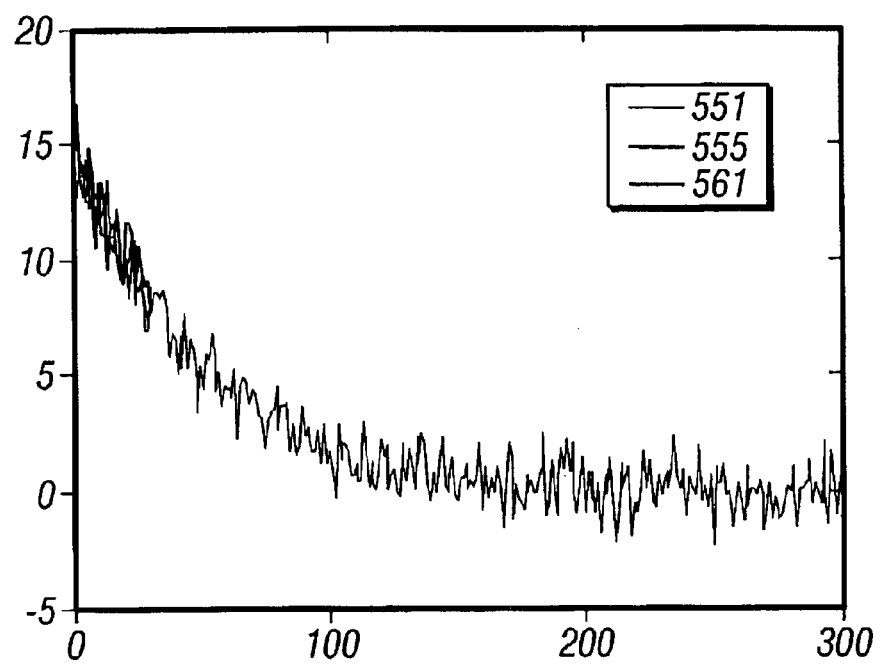
FIG. 10 shows the use of a subset of the data from FIG. 9 for determination of effective porosity.
Figure 10B:
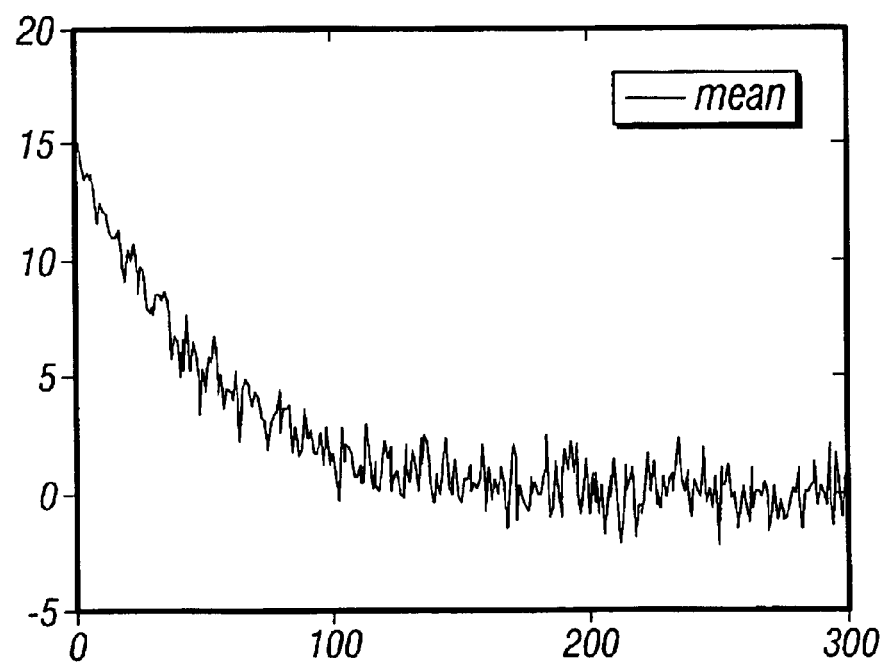
Figure 11A:
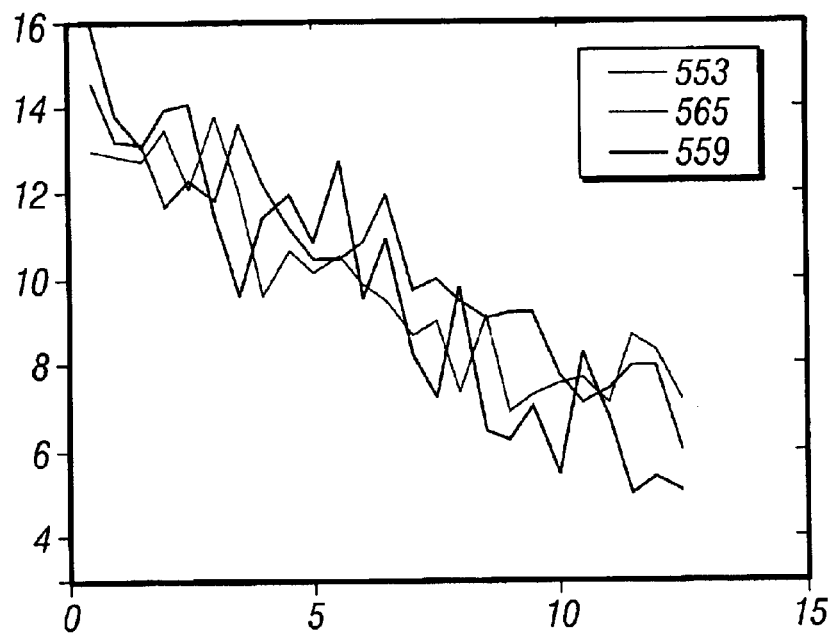
FIG. 11 shows the use of a subset of the data from FIG. 9 for determination of clay bound water.
Figure 11B:
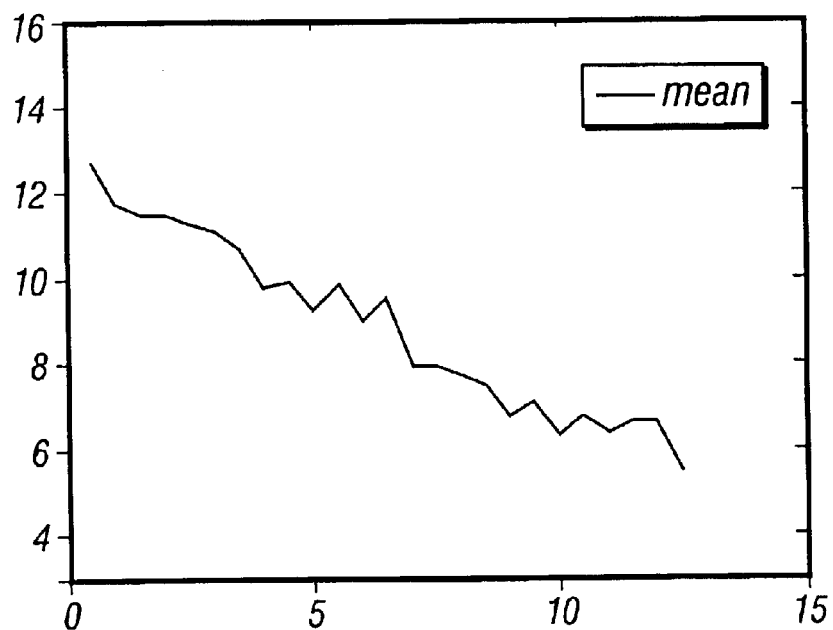

Depending upon the desired objective, portions of the data acquired using the pulse sequences shown in FIG. 7 may be used to provide estimates of the desired properties. For example, if effective porosity is desired, then data from the first block at each frequency of FIG. 9 may be used, i.e., 551, 555, 561, 571, 575 and 581 are used. The results are shown in FIGS. 10a, 10b. Shown in FIG. 10a are a superposition of the echoes (PAP averaged) while FIG. 11b shows the combination. As can be seen, the early portion of the echo sequence has a much improved SNR in FIG. 11b compared to FIG. 11a.

Figure 9:
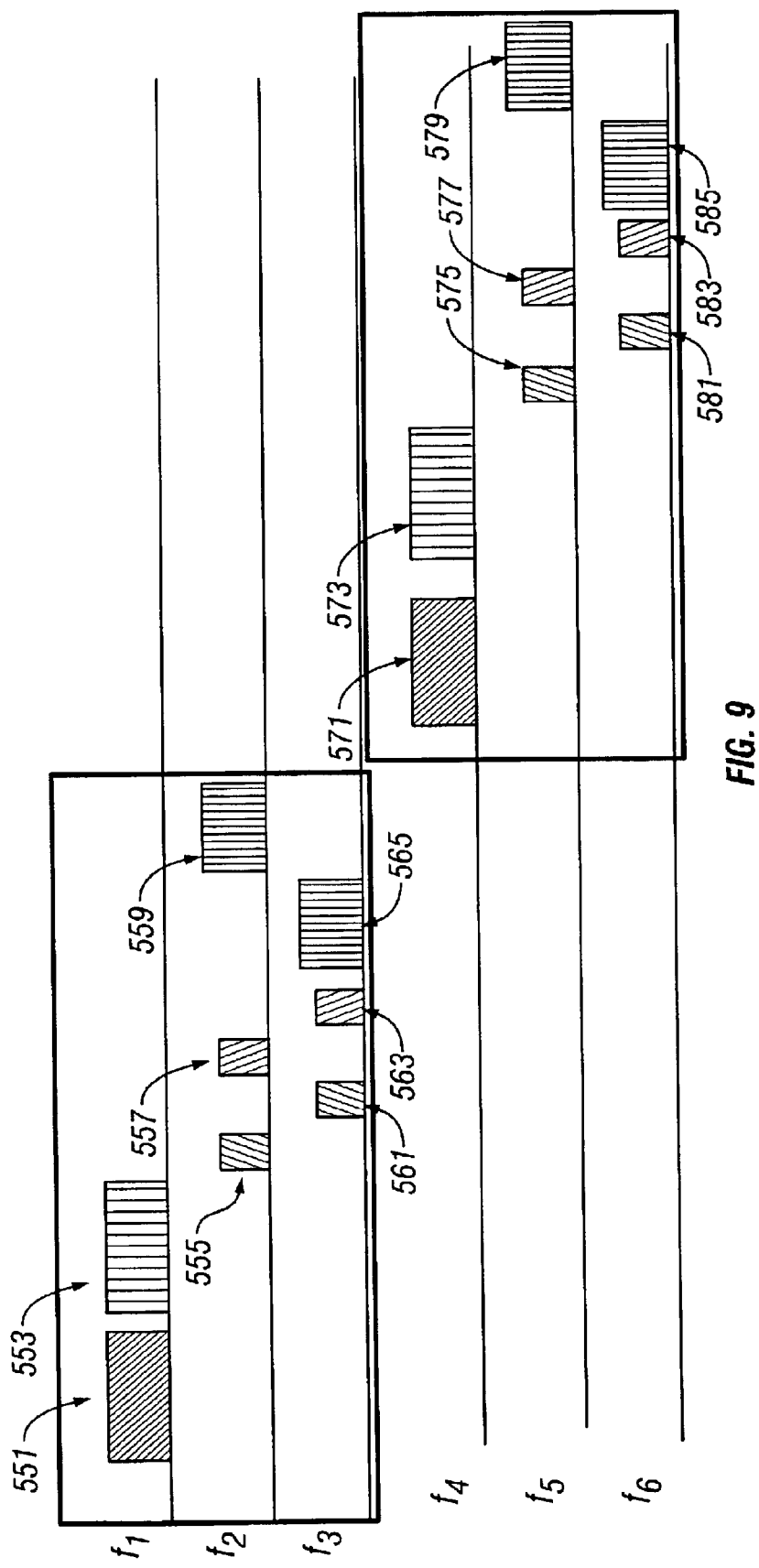
FIG. 9 shows an embodiment at six frequencies for the example of FIG. 7. The PAP is not shown for clarity.

The data acquired using the pulse sequences in FIG. 9 may also be used to determine CBW. In order to do this, data from 553, 559 and 565 (and from the phase alternated set 573, 579 and 565) are processed. FIG. 11a shows the separate results of the PAP averaging while FIG. 11b shows the result of averaging all the data in FIG. 11a. The overall SNR is much improved. Because these trainlets are acquired in PAP patterns, no cross-depth-interval averaging is required if SNR is adequate after averaging these three sets of trainlets. Therefore, the CBW results can be delivered at the highest vertical resolution the tool can provide, i.e., approximately equals to the aperture length.

Figure 12C:
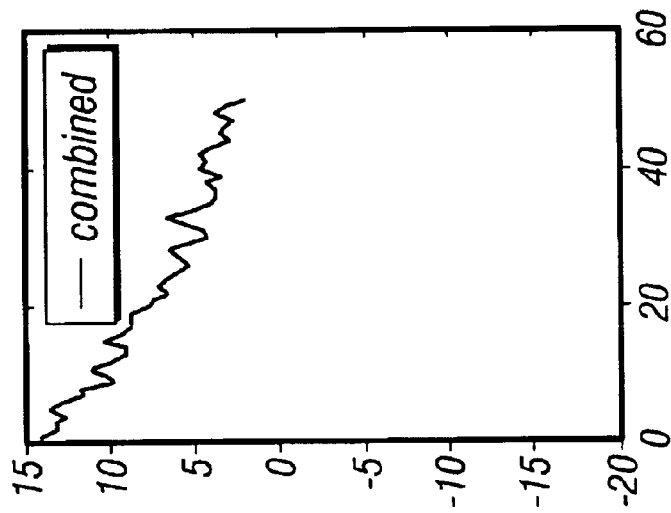
FIG. 12 shows the use of a subset of the data from FIG. 9 for determination of bound volume irreducible.
Figure 12B:
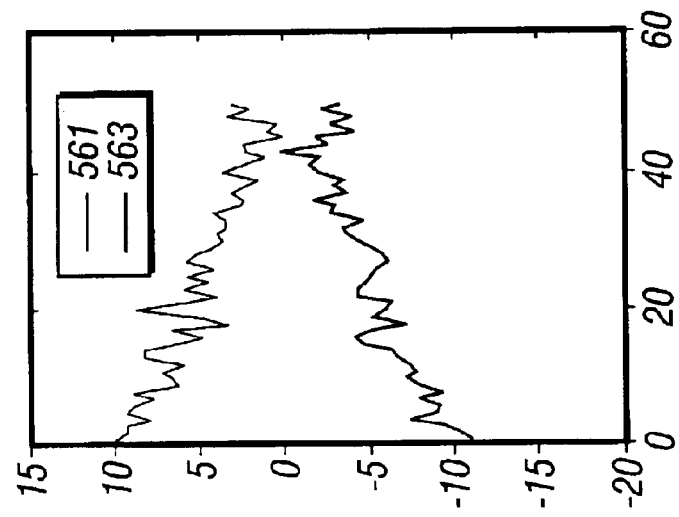
Figure 12A:
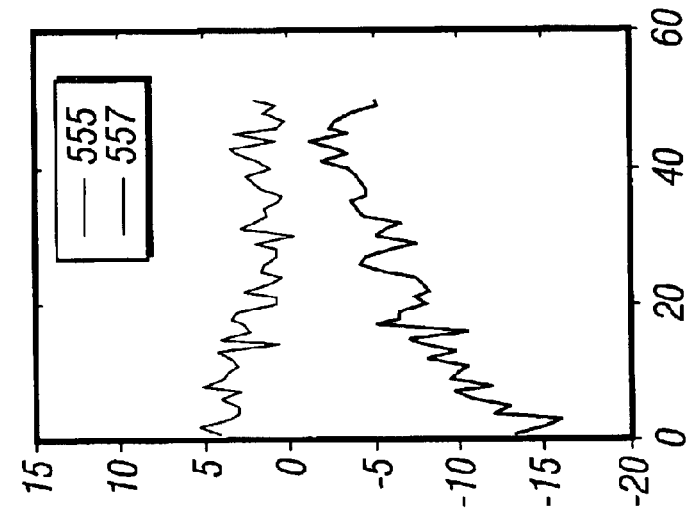

Yet another subset of the data obtained with the FE acquisition may be used to obtain high resolution measurements of BVI. This is illustrated in FIGS. 12a–12c. Shown in FIG. 12a are data from 555 and 557 on the same plot. As noted above in the discussion of FIG. 7 and the corresponding portions of FIG. 9, 555 is fully polarized but 557 is partially polarized. However, because polarization of magnetization does not affect the systematic noise such as DC offset and ringing, they can be treated used in a PAP combination. Because there is only a short wait time between the two sequences, cross-depth-range averaging would be needed to combine these two echo trains. The objective for these echo trains is to obtain BVI, which are fast relaxing components and thus are fully polarized at both the long and short wait times used for 555 and 557, respectively. The cross-TW PAP averaging is not used in prior art methods. Shown in FIG. 12b are data from 561 and 563 which similarly comprise a PAP. The combined data are shown in FIG. 12c. Furthermore, these two PAP combined data sets (555/557 and 561/563) can be averaged together because they are acquired at approximately the same time: stacking together has little effect on vertical resolution but improves SNR significantly. Data from the other frequencies $f_4$, $f_5$ and $f_6$ may be processed similarly. Sometimes, the data quality may still be unsatisfactory even after the averaging of four samples (555/557 and 561/563). In the method of the present invention, additional similar data acquired from different frequencies ($f_4$-$f_6$, etc) can be combined with those from $f_1$-$f_3$. Although this will reduce the vertical resolution, this reduction in vertical resolution is much less than that in prior art methods, where PAP is achieved by combination across several depth ranges. The benefit of the present method is more noticeable for acquisition at 9 and 12 frequencies.

Figure 13:
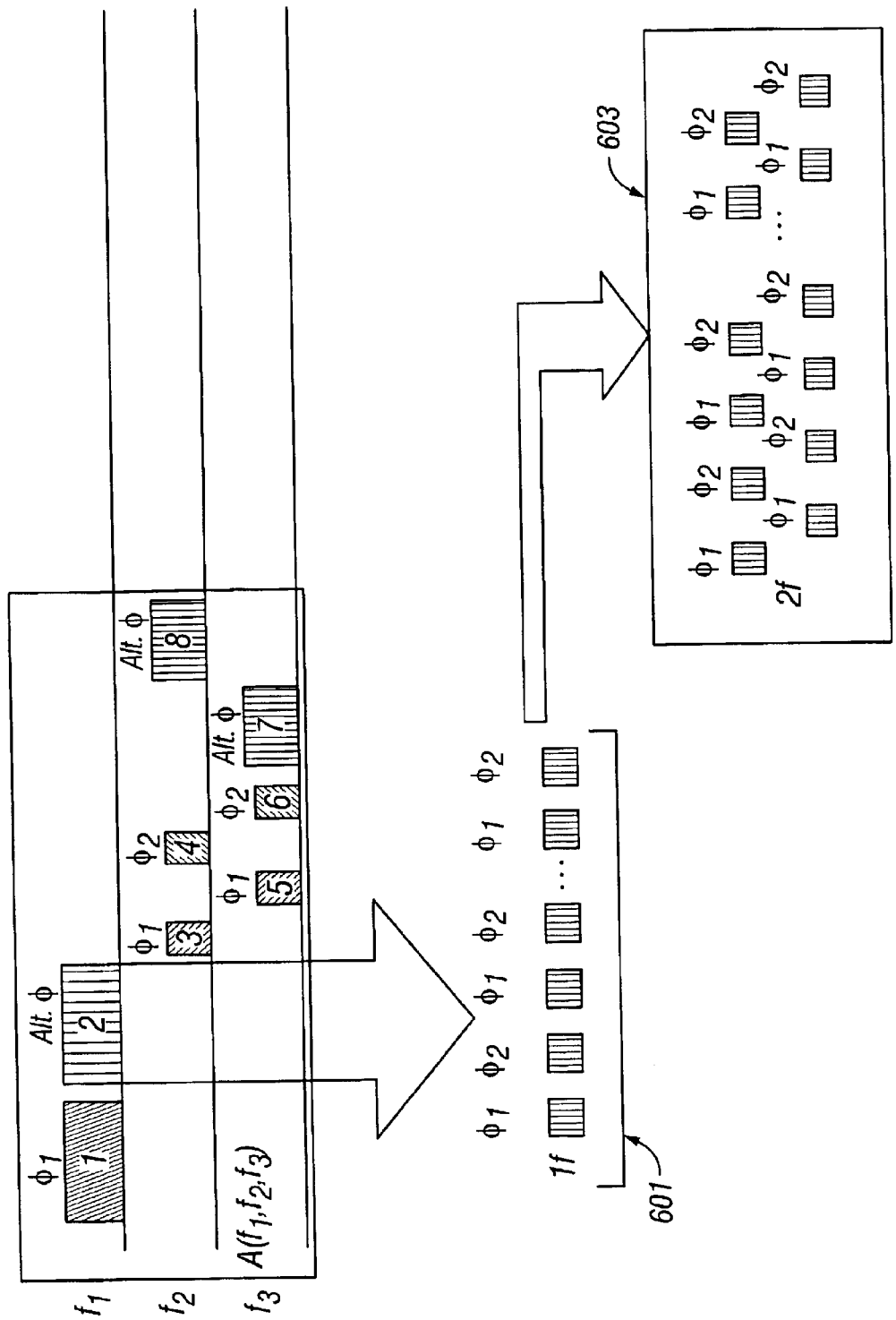
FIG. 13 shows an alternate embodiment of the example of FIG. 9.

In alternate embodiments of the invention, the trainlet sequences denoted by 403 or 503 may be expanded further. This is depicted in FIG. 13 wherein the trainlet sequence may be extended in time (denoted by 601) or may even be split up into multiple frequencies and optionally extended in time (denoted by 603). The same may be done with the short sequences 505, 507, 511, 513 (i.e., they may be expanded to more frequencies or extended in time.

In yet another embodiment of the invention, the individual trainlet sequences may not have the same inter-echo time TE; for instance, a trainlets having NS=16 can be made up of four trainlets with a series of small increment n TE values, with $TE_1 = TE_{min}$, and $TE_n < 2 \cdot TE_{min}$, i.e., TE=0.4, 0.5, 0.6, and 0.7 ms, respectively with a phase alternation within each frequency. This is particularly suitable for improving the estimation of ultra-short relaxation components that are of the order of shortest TE.

Figure 14:
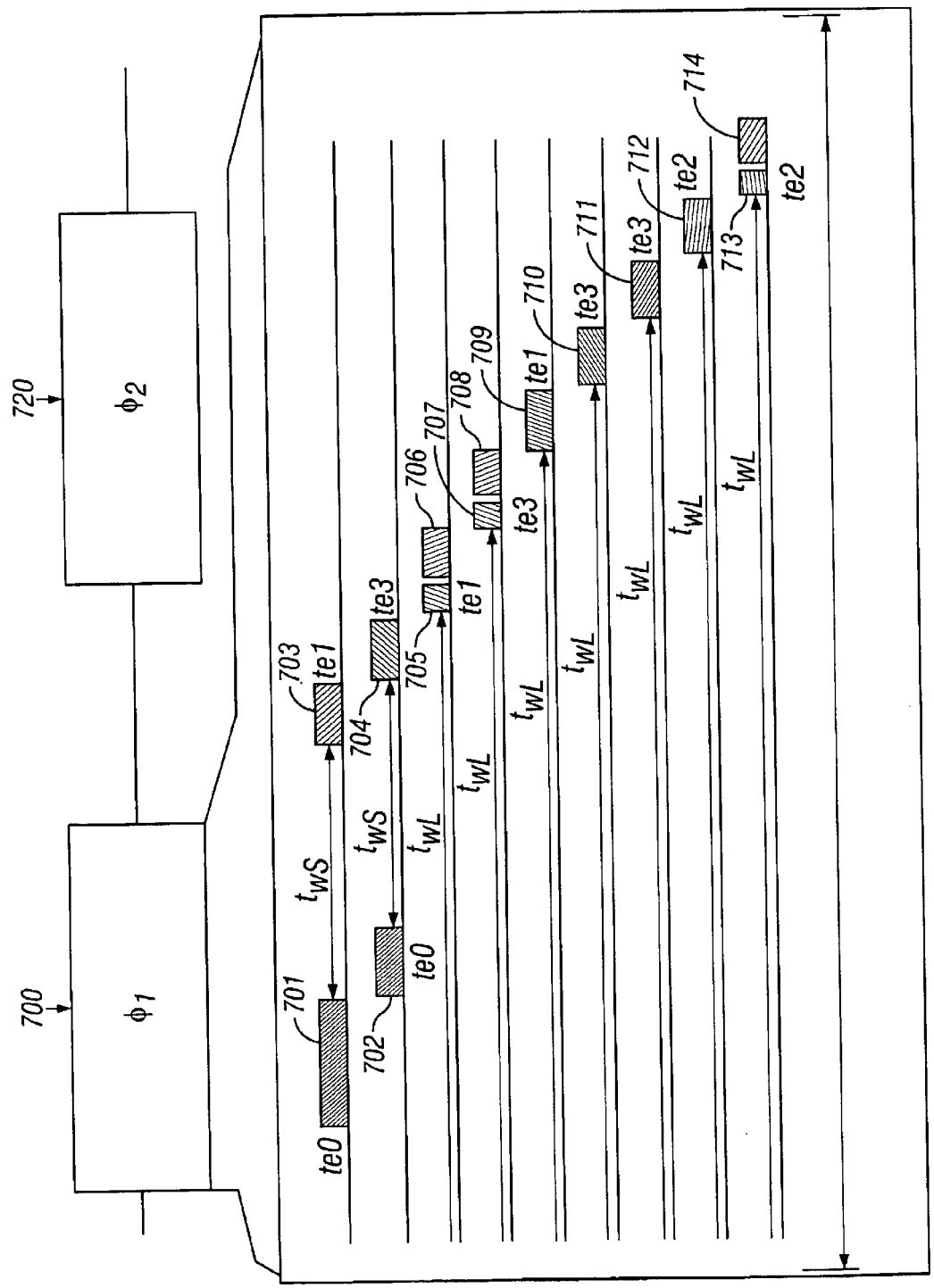
FIG. 14 schematically illustrates an embodiment of the invention for formation evaluation and hydrocarbon evaluation.

When the objective is determination of formation rock properties of an oil well and hydrocarbon typing (including hydrocarbon saturation, viscosity and oil water contact or "OWC") the pulse sequence must satisfy several conditions. As noted above, getting the formation rock properties and other fast relaxing components requires good estimation of early echoes (short relaxation times). Differentiation between light hydrocarbon and water requires two wait times and determination of viscosity may be done with multiple TEs. The combination of using multiple TE and multiple TW is generally preferred for discernment of hydrocarbon phase from wetting phase (water), and to quantify various hydrocarbon properties. Two subsets of multiple TE and multiple TW logging sequences are used in the present invention for hydrocarbon reservoirs dominated with light to moderate light grade oil, or dominated gas or highly volatile oils or condensates, respectively. Although both embodiments takes advantage of $T_1$ and diffusivity contrasts to differentiate fluid phases, one of the embodiments applies to cases where $T_1$ contracts is more useful than the diffusivity contrast. In the other embodiment, the diffusivity contrast is more useful to differentiate the hydrocarbon properties. In terms of the number of TEs and TWs used in the acquisition building blocks, the former uses $N_{TW} > N_{TE}$ and the latter uses $N_{TE} > N_{TW}$. The two embodiments are applicable for a majority of hydrocarbon reservoir NMR logging jobs, therefore, the method of the present invention frees the wellsite engineer from the burden of needing to determine the numbers of TEs and TWs to run and choosing the parameters. FIG. 14 shows an example of an acquisition sequence that satisfies these conditions.

Shown in FIG. 14 is an exemplary sequence for FE+Oil. For illustrative purposes, acquisition at nine frequencies is shown. The blocks 700, 701 represent a basic acquisition sequence 700 that is repeated with an alternated phase at 701. Shown below is a detail of 700. The basic requirement for differentiating water from oil is satisfied by two wait times: blocks 703 and 704 have a short wait time while 705, 707, 709, 710, 711, 712, 713 have a long wait time. Data are acquired with four different values of TE as shown in the figure. In the example shown, 701, 702, 706, 708, 714 are trainlet sequences as described above. 703, 704, 709, 710, 711, 712, are regular sequences and 705, 707, 713 are short sequences. The addition of the trainlets distinguishes the acquisition sequence from prior art dual wait time methods that are primarily aimed at hydrocarbon typing and do not provide complete information about the rock properties. The multiple TE data is useful in determination of viscosity.

In a preferred embodiment of the invention, the trainlet sequences are distributed over at least four frequencies. The trainlet sequences all have the same TE and preferably at least forty echoes are obtained with the entire suite of trainlet sequences. This is helpful in improving the SNR of the early echoes. The short sequences are at the same frequencies as short ones of the trainlet sequences to give a total time for the combination of short sequences and the short ones of the trainlet sequences comparable to a time of a regular sequence. At least two different wait times are used.

Those versed in the art would recognize that in the real world, there is always a field gradient present in the region of examination of a multifrequency logging tool. The observed transverse relaxation time of a fluid filled formation is given by eq. (2), where the first two terms on the right hand side are related to bulk relaxation and surface relaxation while the third term is a diffusion term related to the field gradient G by eq. (3) where C is a constant and D is the diffusivity of the fluid. In an alternate embodiment of the invention, the TEs are selected to provide a contrast in the product TE G.

Table I summarized values of the different parameters in the FE+Oil sequence while Table II gives an example of the parameters used in the embodiment shown in FIG. 14

TABLE I

Input parameters for FE + Oil sequence

| Required every time | | | Required if using values other than default | | |
|---|---|---|---|---|---|
| Parameter | Range | Default | Parameter | Range | Default |
| $TW_L$ | >4 s | Automatic | $TW_S$ | .4–2 s | 1 s |
| $NE|TE_1$ | 360–1000 ms | 500 | $TE_2$ | 1–3 ms | 2 or 2.5 ms |
| Fluid type | Oil or light oil | Oil | $TE_3$ | 3–6 ms | 4 ms |
| $TE_1$ | >1.5 ms | 1.5 ms | | | |

TABLE II

Example of values used in FIG. 14.

| ID | PAP between trains in trainlets | Frequency | TE (ms) [default] | Defaults NE · TE (ms) | NS per level | TW between trainlets |
|---|---|---|---|---|---|---|
| 701 | Y | H | $TE_0$ [0.5] | 10 | 12 | 30 |
| 702 | Y | B | $TE_0$ [0.5] | 10 | 12 | 30 |
| 703 | N | H | $TE_1$ [0.5] | 500 | 1 | |

TABLE II-continued

Example of values used in FIG. 14.

| ID | PAP between trains in trainlets | Frequency | TE (ms) [default] | Defaults NE · TE (ms) | NS per level | TW between trainlets |
|---|---|---|---|---|---|---|
| 704 | N | B | TE$_3$ [4.0] | 500 | 1 | |
| 705 | N | G | TE$_1$ [0.5] | 40 | 1 | 30 |
| 706 | Y | G | TE$_0$ [0.5] | 10 | 10 | 30 |
| 707 | N | D | TE$_3$ [4.0] | 40 | 1 | 30 |
| 708 | Y | D | TE$_0$ [0.5] | 10 | 10 | |
| 709 | N | I | TE$_1$ [0.5] | 500 | 1 | |
| 710 | N | A | TE$_3$ [4.0] | 500 | 1 | |
| 711 | N | C | TE$_3$ [4.0] | 500 | 1 | |
| 712 | N | E | TE$_2$ [3.0][2.0] | 500 | 1 | |
| 713 | N | F | TE$_2$ [3.0][2.0] | 40 | 1 | |
| 714 | Y | F | TE$_0$ [0.5] | 10 | 10 | 30 |

Where two default values are shown (713, 714), the first is for low Gas-Oil Ratio (GOR) oil and the second is for high GOR oil. The frequencies shown are for a nine-frequency tool such as the MRIL® of Numar Corporation with A being the highest frequency and I the lowest frequency. As would be known to those versed in the art, the logging speed is limited by the required pre-polarization time. If long echo trains are being acquired, the number of frequencies can be less than the maximum number available.

Figure 15:
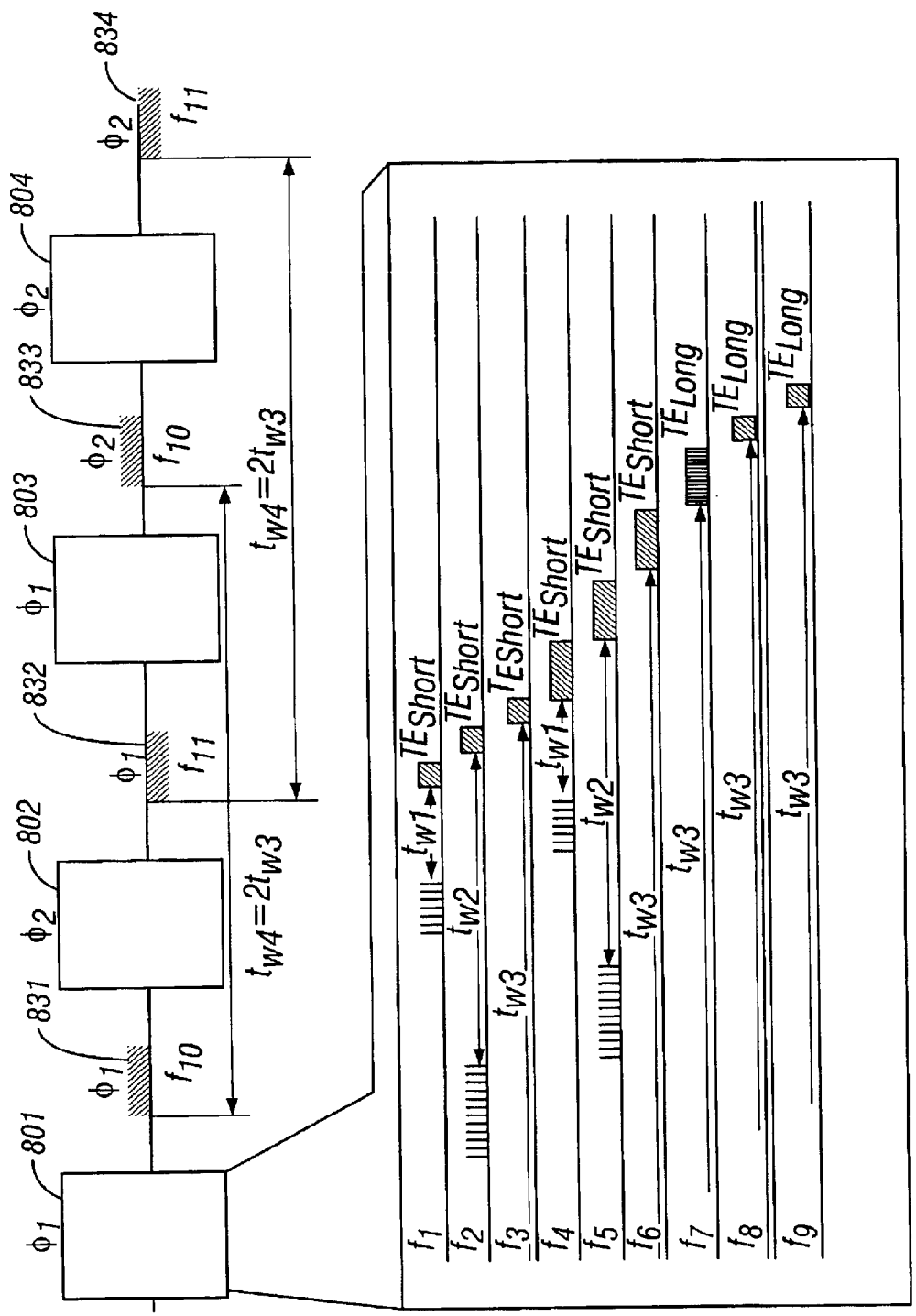
FIG. 15 schematically illustrates an embodiment of the invention for formation evaluation and gas evaluation
Figure 16:
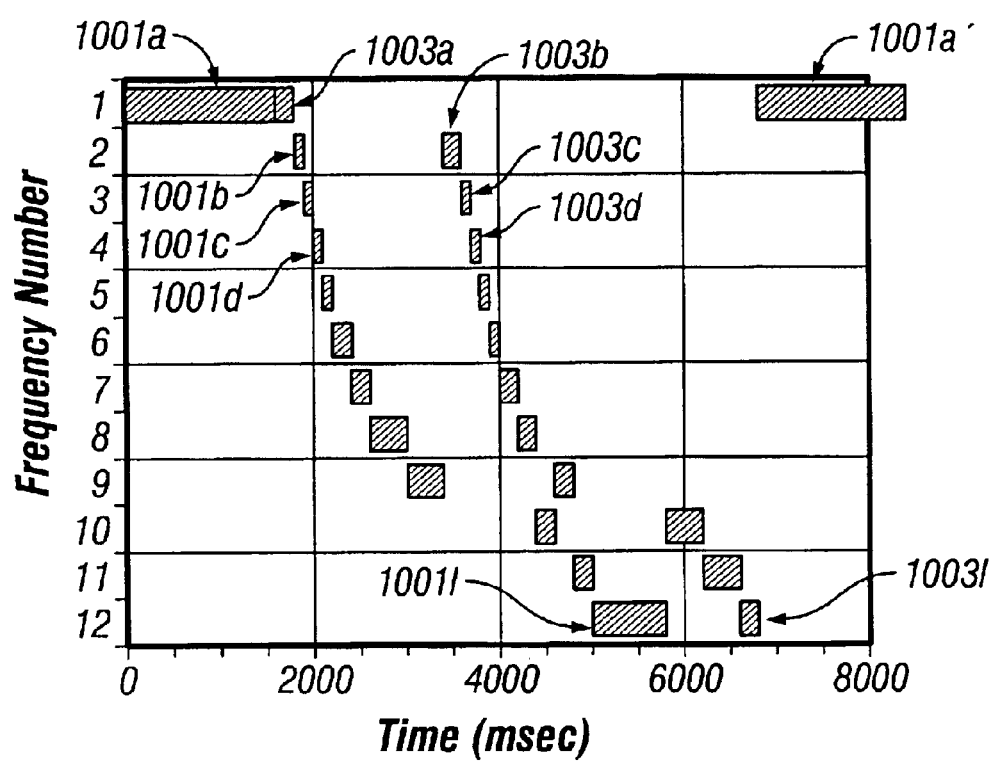
FIG. 16 shows an embodiment of the invention wherein trainlets are used in conjunction with a constant resolution, multifrequency pulse sequence.

When the reservoir is a gas reservoir or one with a volatile condensates, T1 of these hydrocarbon types are usually longer than both oil and water. The objectives are to determine the formation rock properties and the flushed zone hydrocarbon saturation. This can be accomplished with a multiple wait time, dual TE acquisition. Because the exact gas compositions, pressure, or GOR or condensates properties are difficult to obtain a priori, there is considerable uncertainty in T1; hence more TW values are used. In one embodiment, dual pulse sequence cycling method is implemented to assure full polarization of the gas while maintaining logging speed and vertical resolution. In the embodiment, most of the echo trains are acquired with adequately long TW, however, due to the uncertainty in $T_1$, wait-time-doubling cycle as shown by blocks (831 and 833), and blocks (832 and 834) is also used for two frequency acquisitions, which is used to assure fully polarization. As seen in FIG. 15, the acquisition comprises four sub-sequences denoted by 801, 802, 803, 804, a detail of block 801 being shown in the lower portion of the figure. Each of the sequences may be done at at least three frequencies; nine frequencies are shown in the example. In the example shown, the acquisition at the nine frequencies includes three different wait times and two different TEs. Included within the nine frequencies are trainlets, short sequences and long sequences. In order to maintain logging speed, two additional frequencies are used with acquisition denoted by regular sequences 831, 832, 833, 834. PAP acquisition is done as indicated, the pairs being (831, 833) and (832, 834). The wait time for the additional PAP pairs is, in the preferred embodiment of the invention, twice the longest wait time within the individual blocks 801–804. The extra long wait time is necessary to obtain signals from the gas with large polarization In another embodiment of the invention, the pulse sequence is directed towards a constant resolution, multi-frequency acquisition in combination with trainlets as discussed above. A constant resolution, multifrequency acquisition is described in co-pending U.S. patent application Ser. No. 09/778,554 of Edwards, the contents of which are fully incorporated herein by reference. Referring now to FIG. 16, an example of acquisition at twelve frequencies is shown. 1000a, 1001b, 1001c . . . 1001l denotes a constant resolution, multifrequency acquisition sequence as described by Edwards. This is combined with trainlets 1003a, 1003b, 1003c . . . 1003l that provide information regarding CBW. Trainlets 1003a, 1003b . . . 10003l are of the form shown in FIG. 3 with optional modifications previously discussed. Echo trains 1001a, 1001b . . . 1001l, and 1001a' are CPMG sequences similar to 401 in FIG. 3. Also shown in FIG. 16 are pulses 1001a' at the first frequency that comprises a repeat of the constant resolution acquisition. There is a wait time TW between the trainlet 1003a and 1001a'. For simplifying the illustration, the pulses at the remaining frequencies are not shown. The wait times for repeats of 1001a, 1001b . . . 1001l are determined by the trainlets, 1003a, 1003b, 1003c . . . 1003l respectively. In the copending application of Edwards, the wait times can not be made substantially equal. However, in this embodiment, the wait times for the repeats of 1001a, 1001b . . . 1001l are made substantially equal with the addition of the trainlets.

The objective oriented data acquisition of the present invention makes it possible to determine formation and/or fluid properties using known methods. Details of the acquisition parameters have been discussed above. In summary, the objectives discussed above are based on knowledge of at least a portion of the $T_1$ and $T_2$ distribution and of the diffusivity of the fluids. Specifically, from the multiple TW echo trains acquired in an objective oriented package, we obtain the signal build up as the function of TW, from which the $T_1$ distribution may be obtained. From the individual or combined echo trains, the $T_2$ distribution may be obtained. From the knowledge of $T_1$ and $T_2$, the $T_1/T_2$ ratio can be determined. From the multiple TE and multiple frequency echo trains acquired in an objective oriented package, we obtain the magnetization decay as a function of the product (gradient*TE), from which we obtain the decay rate due to the fluid distribution in gradient magnetic field. From this decay we obtain the diffusivities associated with the fluids. See equations (1)–(3) above. The gradient strength necessary for the diffusion determination is known a priori for a given magnet configuration.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of using am NMR instrument conveyed in a borehole the method comprising:
   (a) defining a petrophysical objective for use of the NMR instrument;
   (b) defining at least three building blocks including:
      (i) a first building block of a sequence of trainlets, each trainlet having an excitation pulse and at least one refocusing pulse, and
      (ii) at least two additional building blocks of pulse sequences, each of said at least two additional building blocks comprising an excitation pulse and at least one refocusing pulse and having a duration longer than a duration of one of said trainlets;
   (c) based on said petrophysical objective, selecting said first building block and at least one of said at least two additional building blocks and defining therefrom an acquisition sequence; and
   (d) using said defined acquisition sequence on said NMR instrument and producing signals.

2. The method of claim 1 wherein said at least two additional building blocks are selected from the group consisting of (i) a regular sequence, and (ii) a short sequence;
   wherein said regular sequence and said short sequence comprise a refocusing pulse having a tipping angle that is either substantially equal to 180° or between 90° and 180°.

3. The method of claim 1 wherein said defined acquisition sequence comprises:
   (i) a regular sequence at each of said plurality of frequencies defining a constant resolution sequence; and
   (ii) at least one trainlet at each of said plurality of frequencies.

4. The method of claim 1 wherein each of said trainlets comprises an excitation pulse and a plurality of refocusing pulses and having a total length less than 15 ms, successive ones of said trainlets spaced apart by less than 40 ms.

5. The method of claim 4 wherein trainlets at a first of said plurality of frequencies are interleaved with trainlets at a second of said plurality of frequencies.

6. The method of claim 4 wherein said acquistion sequence comprises trainlets at a plurality of frequencies and wherein a time interval between refocusing pulses of a trainlet at one of said plurality of frequencies is different from a time interval between refocusing a trainlet at another of said plurality of frequencies.

7. The method of claim 4 wherein said blocks of pulse sequences comprises a plurality of frequencies and wherein a proudct of a time internval between refocusing pulses of siad pulse sequences and a gradient of a said static magnetic field at one of said plurality of frequencies is different from product of a time interval between refocusing pulses of said pulses sequences and a gradient of said static magnetic field at another of said plurality of frequencies.

8. The method of claim 1 wherein said acquisition sequence further comprises a plurality of frequencies.

9. The method of claim 1 wherein said at least two additional building blocks are selected from the group consisting of (i) a regular sequence, and, (ii) a short sequence.

10. The method of claim 1 further comprising receiving said signals and estimating therefrom a parameter of interest of at least one (i) said formation, (ii) a fluid in said formation.

11. The method of claim 10 wherein said petrophysical objective includes formation evaluation (FE).

12. The method of claim 11 wherein the acquisition sequence includes phase alternated trainlets.

13. The method of claim 12 further comprising selecting a logging speed to provide high resolutio measurments.

14. The method of claim 11 wherein said acquisition sequence comprises three frequencies.

15. The method of claim 14 wherein said acquisition sequence further comprises:
   (A) a regular sequence and a plurality of trainlets at a first of said three frequencies,
   (B) a first short sequence, a second short sequence and a plurality of trainlets at a third of said three frequencies, and
   (C) a first short sequence, and second short sequence and a plurality of trainlets at a second of said three frequencies.

16. The method of claim 15 wherein at least one of said plurality of trainlets at the first, second and third frequencies comprise phase alternated pairs.

17. The method of claim 15 wherein the first short sequences at
   the second and third frequencies have a longer wait time than the first short sequence at the second and third frequencies respectively.

18. The method of claim 15 wherein the second short sequences at
   the second and third frequencies have a longer wait time than the first shore
   sequence at the second and third frequencies respectively.

19. The method of claim 15 wherein the sequence jas a length less than 1 second comprises a plurality of refocusing pulses having an interval than 2 ms.

20. The method of claim 15 wherein at least one of the plurality of trainlets has a length less than 10 ms and comprises a plurality of refocusing pulses having an interval less than 1 ms.

21. The method of claim 15 wherein at least one of the short sequences has a length less than 40 ms.

22. The method of claim 15 wherein a wait time before said first short sequences is sufficient to substantially polarize nuclear spins in water in the formation.

23. The method of claim 15 wherein a wait time before said second short sequences partially polaries nuclear spins in water in the formation.

24. The method of claim 15 wherein the acquisition sequence further comprises at least one repetition of (A)–(C), said at least one repetition including a phase reversal of a carrier at said three frequencies.

25. The method of claim 15 wherein said acquisition sequence further comprises three additional frequencies, the acquistion sequence 10/288,115 further comprises at least one repetition (A)–(C), said at least one repetition including a phase reversal of a carrier at said three additional frequencies.

26. The method of claim 15 further comprising determining a parameter of interest that is at least one of (i) total porosity, (ii) clay bound water, (iii) effective porosity, (iv) bound volume irreducible (BVI) and determining said parameter of interest comprises processing a sbset of said spin echo signals.

27. The method of claim further comprising determining a bound
   volume inducible (BVI) by processing a subset of spin echo signals and obtaining a high resolution estimate of said parameter.

28. The method of claim 15 wherein any of said plurality of trainlets at any of the first, second and third frequencies further comprises an additional sequence of trainlets at an additional frequency.

29. The method of claim 11 said parameters of interest includes at least one (i) total porosity, (ii) clay bound water, (iii) effective porosity, (iv) bound volume irreducible, (v) porosity distribution, (vi) a $T_1$ distribution, and, (vii) a $T_2$ distribution.

30. The method of claim 1 wherein said objective includes at least one of (A) formation evaluation (FE), and (B) hydrocarbon typing, and the method further comprises determining at least one of (i) hydrocarbon saturation, (ii) viscosity, (iii) a position of an oil-water contact, (iv) diffusivity, (v) a $T_1$ distribution, and, (vi) a $T_2$ distribution.

31. The method of claim 30, further comprising processing said spin echo signals to evaluate at least one of (A) a contrast in a longitudinal relaxation time $T_1$ of fluids in said formation, (B) a contrast in diffusivity of fluids in said formation, (C) a contrast in a ratio of a longitudinal relaxation time $T_1$ and a transverse relaxation time $T_2$ of fluids in said formation.

32. The method of claim 30 wherein said acquisition sequence comprises at least three frequencies.

33. The method of claim 30 wherein said acquisition sequence comprises:
 (A) at least three trainlet sequences having a first TE,
 (B) at least two short sequences at two different frequencies,
 (C) at least two regular sequences having a short wait time at two different frequencies,
 (D) at least two different regular sequences having a long wait time at two different frequencies, wherein the sequences in (B)–(D) comprise at least two TEs different from the TE in (A).

34. The method of claim 1 wherein said objective includes formation evaluation (FE) and gas evaluation.

35. The method of claim 34 wherein said pulse sequence further comprises: 10/288,115
 (A) a pair of phase alternated sub-sequences, each of said sub-sequences comprising a plurality of frequencies, each of said sub-sequences comprising at least two of said at least three building blocks, and
 (B) at least additional regular sequences at at least one additional frequency different from any of said plurality of frequencies, said at least one additional regular sequence interposed between successive ones of said sub-sequences.

36. The method of claim 35 wherein the at least one regular sequence comprises a regular PAP sequence.

37. The method of claim 35 wherein the at least one additional frequency comprises two additional frequencies.

38. The method of claim 35 wherein each of the sub-sequences comprises at least two different wait times and at least two different TEs.

39. The method of claim 34 further comprising determining at leat one (i) a gas saturation of a fluid in the formation, (ii) a diffusivity, (iii) a $T_1$ distribution, and, (iv) a $T_2$ distribution.

40. A method of using a NMR instrument conveyed in a borehole in a formation, the method comprising:
 (a) defining at least three building blocks including:
  (i) a first building block of a sequence of trainlets, each trainlet having an excitation pulse, at least one refocusing pulse, and
  (ii) at least two additional building blocks of pulse sequences, each of said at least two additional building blocks comprising an excitation pulse and at least one refocusing pulse and having a duration longer than a duration of one of said trainlets;
 (b) selecting said first building block and at least one of said at least two additional building blocks and defining therefrom an acquisitioin sequence comprising a plurality of frequencies;
 (c) using said defined acquistion sequence for pulsing a radio frequency (RF) antenna on the NMR instrument and proudcing signals from the formation;
 (d) receiving said signals; and
 (e) processing said received signals to determine a parameter of interest selected from (i) total porosity, (ii) clay bound water, (iii) effective porosity, (v) bound volume irreducible (v) a porosity distribution, (vi) a $T_1$ distribution, and, (vii) and $T_2$ distribution.

41. The method of claim 40 wherein said plurality of frequencies comprises three frequencies 10/288,115 .

42. The method of claim 41 wherein said acqisition sequence further comprises:
 (A) a regular sequence and a plurality of trainlets at the first frequency,
 (B) a first short sequence, a second short sequence and a plurality of trainlets at the third frequency, and
 (C) a first short sequence, a second short sequence and a plurality of trainlets at the second frequency.

43. The method of claim 41 wherein at least one of said plurality of trainlets at the first, second and third frequencies comprise phase alternated pairs.

44. The method of claim 41 wherein the first and second short sequence at each of the second and third frequencies comprise phase alternated pairs.

45. The method of claim 41 wherein the second short sequence at the second and third frequencies have a longer wait time than the first shoret sequence at the second and third frequencies respectively.

46. The method of claim 41 wherein the regular sequence has a length less than 1 second comprises a plurality of refocusing pulses having an interval than 2 ms.

47. The method of claim 41 wherein a wait time before said first short sequences is sufficient to substantially polarize nuclear spins in water in the formation.

48. The method of claim 41 wherein said plurality of frequencies comprises three additional frequencies, the acqustion sequence further comprises at least one repetition of (A)–(C), said at least one repetition including a phase reversal of a carrier at said three additional frequencies.

49. The method of claim 41 further comprises processing a subset of said spin echo signals and obtaining a high resolution estimate of said parameter.

50. The methof of claim 40 wherein a time interval between refocusing pulses of a pulse sequence at one of said plurality of frequencies is different from a time interval between refocusing pulses of a pulse sequence at another of said plurality of frequencies.

51. The method of claim 40 wherein a product of a time interval between refocusing pulses of a pulse sequence and a gradient of said static magnetic field at one of said plurality of frequencies is different from a product of a 10/288,115 time interval between refocusing pulses of a pulse sequences and a gradient of a said static magnetic field at another of said plurality of frequencies.

* * * * *